United States Patent
Chang et al.

(10) Patent No.: US 6,428,976 B1
(45) Date of Patent: *Aug. 6, 2002

(54) RAPID IDENTIFICATION OF MICROORGANISMS

(75) Inventors: Tsung C. Chang, Taipan; Shiowwen Chen; Hwia C. Ding, both of Hsinchu, all of (TW)

(73) Assignee: Food Industry Research and Development Institute (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/655,132

(22) Filed: Sep. 5, 2000

Related U.S. Application Data

(62) Division of application No. 08/907,696, filed on Aug. 8, 1997, now Pat. No. 6,210,911.

(51) Int. Cl.$^7$ .................. G01N 33/569; C12Q 1/70; C12N 13/00
(52) U.S. Cl. .................. 435/38; 435/4; 435/5; 435/7.37; 435/29; 435/30; 435/34; 435/173.1
(58) Field of Search .................. 435/4, 5, 7.37, 435/29, 30, 34, 38, 173.1

(56) References Cited

U.S. PATENT DOCUMENTS

| | | | | |
|---|---|---|---|---|
| 4,160,205 | A | * | 7/1979 | Hobbs et al. |
| 4,264,728 | A | * | 4/1981 | Wilkins |
| 4,945,060 | A | * | 7/1990 | Turner et al. |
| 5,336,600 | A | * | 8/1994 | Monget |

OTHER PUBLICATIONS

Okrend et al. J. Food Protect. 1990. vol. 53, No. 3, pp. 249–252.*
Ahmed et al. J. Infect. Diseases. 1987. vol. 155, No. 4, pp. 806–809.*
Manual of Clinical Microbiology, 3rd ed. Am. Soc. for Microbiology, Washington, D.C., pp. 491–494, 1980.*
Pelczar et al. Microbiology, 4th ed. McGraw–Hill Book Co. New York, NY, pp. 400–402, 1977.*
Carminati et al., "Application of the Conductance Measurement Technique for Detection of *Streptococcus salivarius* ssp. *thermophilus* Phages", J. Diary Sci 74:1472–1476, (1991).
Dupont et al., "Analytical procedure for use of conductance measurement to estimate *Escherichia coli* in shellfish", J. Applied Bacteriology 77:296–302, (1994).
Franken et al., "Direct and indirect conductimetry for identification and detection of plant pathogenic bacteria", J. Applied Bacteriology, 74:234–242, (1993).
Meng et al., "Detention and control of *Escherichia coli* 0157:H7 in foods", Trends in Food Science & Technology, 5:179–184, (1994).
Ogden, "A conductance assay for the detection and enumeration of *Escherichia coli*", Food Microbiology, 10:321–327, (1993).
Padhye et al., "*Escherichia coli* 0157:H7: Epidemiology, Pathogenesis, and Methods for Detection in Food", Journal of Food Protection 55(7):555–565, (1992).
Ronner et al., "Isolation and Characterization of a Coliphage Specific for *Escherichia coli* 0157:H7", Journal of Food Protection, 53(11):944–947, (1990).
Venkateswaran et al., "Comparison of Commercially Available Kits with Standard Methods for the Detection of Coliforms and *Escherichia coli* in Foods", Applied and Environmental Microbiology, 62(7):2236–2243, (1996).
Wells et al., "Laboratory Investigation of Hemorrhagic Colitis Outbreaks Associated with a Rare *Escherichia coli* Serotype", Journal of Clinical Microbiology, 18(3):512–520, (1983).
Okrend et al., "Isolation and Identification of *Escherichia coli* 0157:H7 from Meat" REVISION 3 OF LABORATORY COMMUNICATION #38 pp. 1–13.
Hitchins et al., "Chapter 4. *Escherichia coli* and the Coliform Bacteria", FDA Bacteriological Analytical Manual, 8th Edition, pp. 4.01–4.29, (1995).
Griffiths, "Enzyme Assays", J. of Dairy Science, 76(10), 3122–2125, (1993).
Stewart et al., "The Bacterial lux Gene Bioluminescent Biosensor Revisited", ASM News, 62(6):297–301, (1996).

* cited by examiner

Primary Examiner—Christopher R. Tate
(74) Attorney, Agent, or Firm—Fish & Richardson P.C.

(57) ABSTRACT

A method of determining whether a test microorganism is a known microorganism, involving use of an agent that specifically affects the growth of the known microorganism. The invention also features a method of identifying *E. coli* 0157:H7 that are based on following criteria: a test microorganism is *E. coli* 0157:H7 if the microorganism is (i) *E. coli*, (ii) incapable of fermenting sorbitol, and (iii) susceptible to infection by AR1 phage.

3 Claims, 1 Drawing Sheet

RAPID IDENTIFICATION OF MICROORGANISMS

This application is a divisional application of U.S. application Ser. No. 08/907,696, filed Aug. 8, 1997, now U.S. Pat. No. 6,210,911.

BACKGROUND OF THE INVENTION

Escherichia coli ("E. coli") O157:H7, first isolated in 1975 from a patient with grossly bloody diarrhea, is now recognized as an important foodborne pathogen (Ministry of Health and Welfare, Information on the Detection of Pathogenic Microorganisms, 1996; Meng et al., Trends Food Sci. Tech. 5:179–185, 1994; Padhye et al., J. Food Prot. 55:555–565, 1992; Riley et al., N. Engl. J. Med. 308:681–685, 1983). In adults, the illness is usually self-limited. However, the more serious hemolytic uremia syndrome ("HUS") affects some of the infected patients, especially children and the elderly. The mortality rate of HUS is 3 to 10%. Most outbreaks have been associated with consumption of undercooked ground beef or raw milk. Cattle has been identified as an important reservoir of E. coli O157:H7. Person-to-person transmission has also been identified in some day-care center and nursing home outbreaks (Centers for Disease Control and Prevention, Morbid. Mortal. Weekly Rep. 42:253–257, 1993; Lior, Dairy Food and Environ. Sanitation 14:378–382, 1994; Padhye et al., J. Food Prot. 55:555–565, 1992).

Several methods have been developed for rapid detection and identification of E. coli O157:H7. Most of these methods are immunoassays for detecting the E. coli 157 somatic antigen (Huang et al., J. Food Prot. 59:170–174, 1996; Meng et al., Sci. Tech. 5:179–185, 1994). Confirmation of a positive result by either biochemical or serological tests, such as Vero cell assay or a test for the presence of H7 antigen, are required.

DNA probes and polymerase chain reaction have also been used to detect E. coli O157:H7 (Meng et al., Sci. Tech. 5:179–185, 1994). Although DNA-based methods are sensitive, there are several major drawbacks. First, they detect the presence of nucleic acid of the target bacteria rather than the viable bacteria themselves. Second, most of the DNA-based methods are designed to detect the genes that encode verotoxin or virulence-associated marker of verotoxin- producing E. coli, and are not specific for E. coli O157:H7. In addition, DNA-based methods are cumbersome and expensive.

A coliphage named AR1 has been found to infect E. coli O157:H7 with high specificity (Ronner et al., Journal of Food Protection 54: 944–947, 1990).

SUMMARY OF THE INVENTION

The invention features a method of determining whether a test microorganism is a known microorganism such as a bacterium (e.g., an enterobacterium such as Escherichia coli), or yeast. The method includes the steps of: (i) providing a first culture that contains the test microorganism and an agent (e.g., a bacteriophage) that specifically affects the growth rate of the known microorganism; (ii) measuring a growth rate-related value of the first culture; and (iii) comparing the value of the first culture with a corresponding value of a second culture, the second culture being identical to the first culture except that the second culture is free of the agent, or contains the known microorganism and is free of the agent; wherein a difference in the two values is an indication that the test microorganism is the known microorganism. Examples of growth-rate-affecting agents include, but are not limited to, AR1 phage for E. coli O157:H7, P22 phage for Salmonella typhimurium (Griffiths, J. Dairy Sci., 76:3118–3125, 1993), and A511 phage for Listeria (Stewart et al., ASM News, 62:297–301, 1996). By "Specifically" is meant that the agent affects the growth of mainly one microorganism. Of course, an agent that has cross-activity to a very limited number (e.g., no more than 3) of other microorganisms may also be used, if additional discerning criteria are available.

Also featured in the invention is a method of determining whether a test microorganism is E. coli O157:H7.

One embodiment of the method includes the following steps: (1) determining whether the test microorganism is E. coli; (2) growing the test microorganism in a medium containing sorbitol; (3) determining whether the test microorganism ferments sorbitol; (4) providing a first culture that contains the test microorganism and AR1 phage; (5) measuring a growth rate-related value of the first culture; and (6) comparing that value of the first culture with a corresponding value of a second (i.e., control) culture that is identical to the first culture except that (a) it is free of AR1 phage, or (b) it is free of AR1 phage and contains any E. coli strain instead of the test microorganism. The test microorganism is indicated as E. coli O157:H7 if (i) it is E. coli, (ii) it is incapable of fermenting sorbitol, and (iii) there is a significant (e.g., at least two-fold) difference in the growth rate-related value between the two cultures.

In another embodiment of the method of this invention, the test microorganism is already known to be E. coli. To determine if this E. coli strain is O157:H7, one can (1) grow the test strain in a sorbitol-containing medium; (2) determine whether the test strain ferments sorbitol; (3) provide a first culture that contains the test strain and AR1 phage; (4) measuring a growth rate-related value of the first culture; and (5) compare that value of the first culture with a corresponding value of a second culture which is identical to the first culture except that (a) it is free of AR1 phage, or (b) it contains any other E. coli strain and is free of AR1 phage. The test strain will be identified as E. coli O157:H7 if (i) it is incapable of fermenting sorbitol; and (ii) there is a significant (e.g., at least two-told) difference in the growth rate-related value between the two cultures.

Yet another embodiment of the method is to determine whether a test microorganism incapable of fermenting sorbitol is E. coli O157:H7. This method includes the following steps: (1) determining whether the test microorganism is indicated as E. coli; (2) providing a first culture that contains the test microorganism and AR1 phage; (3) measuring a growth rate-related value of said first culture; and (4) comparing that value of the first culture with a corresponding value of a second culture that is identical to the first culture except that (a) it is free of AR1 phage, or (2) it is free of AR1 phage and contains any E. coli strain. The test microorganism is E. coli O157:H7 if (i) it is E. coli; and (ii) there is a significant (e.g., at least 10-fold, or even 20-fold) difference in the growth rate-related value between the two cultures.

If the test microorganism is already known to be susceptible to AR1 infection, one can conduct the following steps to determine if the microorganism is E. coli O157:H7: (1) determining whether the test microorganism is E. coli; (2) growing the test microorganism in a culture medium containing sorbitol; and (3) determining whether the test microorganism ferments sorbitol. The test microorganism is E. coli O157:H7 if it is E. coli and is incapable of fermenting sorbitol.

In all of the above-described methods, a growth rate-related value includes, but is not limited to, (i) a value of an electrical parameter such as conductance, resistance, or any other proper parameter; (ii) a value derived from values of an electrical parameter, e.g., a time point at each an accelerating change of an electrical parameter occurs (if the electrical parameter is conductance, the time point is herein termed "detection time"; (iii) a value of an optical parameter such as optical density; (iv) a value derived from values of an optical parameter; and (v) certain biochemical indexes that reflect growth of a microorganism. The methods based on use of an electrical or optical parameter allows automated screening of a large number of samples.

Other features and advantages of the present invention will be apparent from the following drawings and description, and also from the appending claims.

DESCRIPTION OF THE PREFERRED EMBODIMENTS

Figure 1:
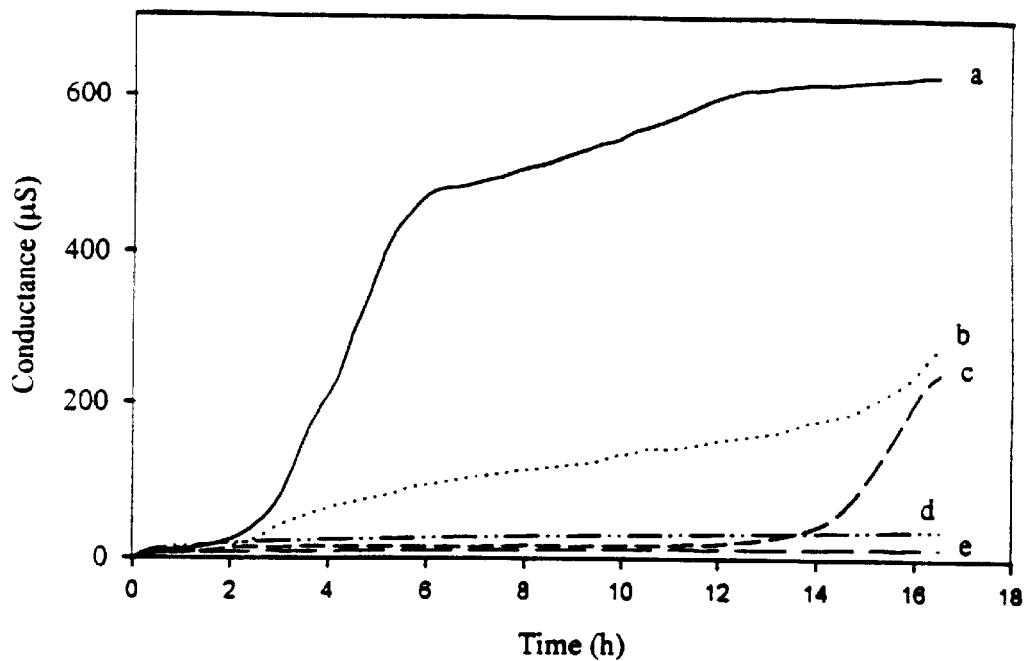
FIG. 1 is a graph showing the effect of cell:phage ratio on the conductance curves of *E. coli* O157:H7 (CCRC13095). Curve (a) was obtained in the absence of phage; and the remaining curves were obtained at the following cell:phage ratios: (b) 1:0.01, (c) 1:0.1, (d) 1:1, and (e) 1:10.

The present invention features methods of determining whether a test microorganism is *E. coli* O157:H7. The invention is based on Applicants' discovery that a test microorganism can be identified as *E. coli* O157:H7 with high (e.g., over 90% or even 98%) certainty if it meets the following criteria: The microorganism must be (1) *E. coli*; (2) incapable of fermenting sorbitol; and (3) susceptible to infection by AR1 phage (e.g., as determined by a conductance-based protocol described below).

Various strains of AR1 phage can be used to practice methods of this invention. A strain of AR1 phage was deposited on Dec. 1, 1994 at the American Type Culture Collection, 10801 University Blvd., Manassas, Va. 20110-2209, U.S.A. The ATCC accession number is 75957.

There are several widely known assays for determining whether a microorganism is *E. coli* (Venkateswaran et al., Applied and Environmental Microbiology, 62: 2236–2243, 1996; Hitchins et al., Chapter 4, in FDA Bacteriological Analytical Manual, 1995; and Okrend et al., Revision 3 of Laboratory Communication #38, pages 1–13, FSIS, Microbiology Division, U.S. Department of Agriculture, Washington, D.C., 1989); conventional biochemical tests or a commercial kit such as API 20E (bioMerieux, Marcy-I'Etoile, France) can be used.

Assays for determining whether a microorganism isolate can ferment sorbitol are well known in the art. In a typical assay, test microorganisms or a sample suspected of containing bacteria (e.g., food, blood, stool, or drinking water) are cultured on MacConkey sorbitol agar to form colonies. If a colony can ferment sorbitol, it will be red; otherwise, it will be white.

To determine whether a microorganism isolate is susceptible to infection by AR1 phage, plaque assay on agar plates can be performed (see, e.g., Ronner et al., supra). Alternatively, the isolate can be used to inoculate an appropriate liquid culture medium together with an appropriate amount of AR1 phage (see the Example, infra). If the microorganism is infectable by AR1 phage, the liquid culture will not reach an exponential growth phase (i.e., log phase), which is characteristic of a healthy culture; or the culture will grow much slower and reach the log phase at a significantly later time (i.e., at least twice or even thrice as long) than a control culture that is free of AR1 phage and is inoculated with an identical or similar (i.e., the difference is no more than 10-fold) concentration of an *E. coli* strain or the microorganism isolate. Thus, an artisan can compare the time for each of the test and control cultures to reach the log phase. If the control culture contains a known *E. coli* strain, the time for it to reach the log phase can be predetermined or estimated from prior art. Alternatively, one can compare a growth rate-related value (such as an electrical or an optical parameter) of the culture with that of the control culture (which can be pre-determined or estimated from prior art) at a given time point. The time point can be empirically pre-determined. If the test culture is infected by AR1 phage, there will be a significant difference in the growth rate-related value between the test and control cultures.

For the purpose of identifying *E. coli* O157:H7, it is preferred to use an electrical parameter (e.g., conductance)-based assay, rather than a plaque assay, to determine a test microorganism's susceptibility to AR1. The former assay not only gives a lower background, but also is easier to be adapted to automation.

The three criteria for identifying *E. coli* O157:H7 can be examined in any order. For instance, one can first grow a test microorganism on MacConkey sorbitol agar to determine if the microorganism is a sorbitol fermenter; if not, one can proceed to further determine if the microorganism is infectable by AR1 phage; if yes, then one can determine if the test microorganism is *E. coli*. Alternatively, one can first determine if the test microorganism is infectable by AR1 phage, then determine if it can ferment sorbitol and last if it is *E. coli*. The three criteria can also be examined concurrently. Or if one or two of the criteria is already known to be met, an artisan can simply test for the remaining criteria or criterion.

Without further elaboration, it is believed that the above description has enabled the present invention to its fullest extent. All citations are incorporated herein by reference. The following specific example is, therefore, to be construed as merely illustrative, and not limitative of the remainder of the disclosure in any way whatsoever.

Identification of *E. coli* O157:H7 Based on a Conductance

Conductance measurements have been used for the determination of total bacterial count Enterobacteriaceae bacteria and other bacteria in food samples (Firstenberg-Eden, R. Food Tech. 37:64–70, 1983; Gibson et al., Int. J. Food Microbiol. 1:127–134, 1984; Hadley et al., Appl. Environ. Microbiol. 34:14–17, 1977; Cousins et al., J. Food Prot. 53:568–570, 1990; Easter et al., J. Hyg. Camb. 94:245–262, 1985; Smith et al., J. Appl. Bacteriol. 67:575–588, 1989). They have also been used for detecting the presence of antibiotics in bacterial cultures (U.S. Pat. No. 5,591,599 to Chang et al.). The principle of these measurements is that multiplication of bacteria in a culture medium will result in an increase in the conductivity of the medium. At a time point ("detection time") when the bacteria concentration reaches approximately $10^7$ cfu/ml, an accelerating increase of conductivity will occur. Detection times are inversely proportional to the initial bacterial count in the test sample (Firstenberg-Eden et al., Impedance Microbiology. pp. 7–90. John Wiley and Sons Inc., New York, 1984).

The technique is particularly useful for rapid screening various foods to determine whether they meet the desired microbiological standards. However, this technique is for the first time used to identify *E. coli* O157:H7 by using AR1 phage which is specific to the microorganism.

Bacterial Strains and Media

All the bacterial strains used herein are listed in Table 1. There were 41 strains of *E. coli* O157:H7 and 155 strains of non-O157:H7 *E. coli*. Among the non-O157:H7 *E. coli* strains, which include food isolates, enteroinvasive *E. coli* ("EIEC"), enteropathogenic *E. coli* ("EPEC"), and enterotoxigenic *E. coli* ("ETEC"), the serotypes of 99 strains were known; and the remaining 56 strains were only tested for O157 antigen by a latex test (Oxoid, Unipath Ltd., Hampshire, UK) and found to be negative.

All the bacterial strains were maintained at 4° C. on tryptic soy agar (Difco Laboratories, Detroit, Mich., USA) except that strains of Vibrio parahaemolyticus were maintained on tryptic soy agar supplemented with 2.5% NaCl.

The following media were used: MacConkey sorbitol agar (Oxoid, Unipath Ltd., Hampshire, UK), 0.1% peptone water, Plate Count Agar (Difco Laboratories, Detroit, Mich.), and Malthus SPYE broth (Malthus Instruments, Crawley, UK).

TABLE 1

| Microorganism | No. of Strains | Source[a] |
|---|---|---|
| *Escherichia coli* O157:H7 | 41 | CRC 13084–99, 14824–5; 15373–4, 15376–7, 15970; H11–18, NCHU; W1, NLFD; LA1, LO3–8, A8993–C32, 933, NTU |
| *E. coli* O113:K75(B19):H21 | 1 | CCRC 14883 |
| *E. coli* O121:H12 | 1 | CCRC 14884 |
| *E. coli* O145:K?(B):H— | 1 | CCRC 14885 |
| *E. coli* O8:K27 -:H— | 1 | CCRC 14909 |
| *E. coli* O26 | 1 | CCRC 14917 |
| *E. coli* O111 | 1 | CCRC 14918 |
| *E. coli* O25:K98:NM | 1 | CCRC 15370 |
| *E. coli* O78:K80:H12 | 1 | CCRC 15371 |
| *E. coli* O124:NM | 1 | CCRC 15375 |
| *E. coli* O1a, 1b: | 1 | CCRC 15479 |
| *E. coli* O2a, 2b:K5 (L):H4 | 1 | CCRC 15480 |
| *E. coli* O3:K2a, 2b (L):H2 | 1 | CCRC 15481 |
| *E. coli* O5:K4 (L):H4 | 1 | CCRC 15482 |
| *E. coli* O6:K2:H1 | 1 | CCRC 15483 |
| *E. coli* O8:K85:K99 | 1 | CCRC 15484 |
| *E. coli* O9:K35:K99 | 1 | CCRC 15485 |
| *E. coli* O11:H4 | 1 | CCRC 15486 |
| *E. coli* O13:K (L):H11 | 1 | CCRC 15487 |
| *E. coli* O14:K (7L):NM | 1 | CCRC 15488 |
| *E. coli* O15:K14 (L):H4 | 1 | CCRC 15489 |
| *E. coli* O16:K1 (L):NM | 1 | CCRC 15490 |
| *E. coli* O17:H16 (L):H18 | 1 | CCRC 15491 |
| *E. coli* O19a, 19b:K:H7 | 1 | CCRC 15492 |
| *E. coli* O20a, 20b:K17 (L):NM | 1 | CCRC 15493 |
| *E. coli* O22:K13 (L):H1 | 1 | CCRC 15494 |
| *E. coli* O26:K60 (B6) | 1 | CCRC 15496 |
| *E. coli* O28a, 28c:K73 (B18):NM | 1 | CCRC 15497 |
| *E. coli* O29:NM | 1 | CCRC 15498 |
| *E. coli* O32:K:H19 | 1 | CCRC 15499 |
| *E. coli* O34:K:H10 | 1 | CCRC 15500 |
| *E. coli* O35:K:H10 | 1 | CCRC 15501 |
| *E. coli* O37:K:H10 | 1 | CCRC 15502 |

TABLE 1-continued

| Microorganism | No. of Strains | Source[a] |
|---|---|---|
| *E. coli* O88:K:H25 | 1 | CCRC 15510 |
| *E. coli* 0101:K30:K99 | 1 | CCRC 15511 |
| *E. coli* O107:K:H27 | 1 | CCRC 15512 |
| *E. coli* O114:K:H32 | 1 | CCRC 15513 |
| *E. coli* O119:K69 (B14) | 1 | CCRC 15514 |
| *E. coli* O124:K72 (B17):H | 1 | CCRC 15515 |
| *E. coli* O139:K82 (B):H1 | 1 | CCRC 15518 |
| *E. coli* O36:K:H9 | 1 | CCRC 15519 |
| *E. coli* O41:K:H40 | 1 | CCRC 15520 |
| *E. coli* O55:B5:H— | 1 | CCRC 15521 |
| *E. coli* O60:K:H33 | 1 | CCRC 15522 |
| *E. coli* O65:K:NM | 1 | CCRC 15523 |
| *E. coli* O70:K:H42 | 1 | CCRC 15524 |
| *E. coli* O77:K:NM | 1 | CCRC 15526 |
| *E. coli* O86a, 86b:K64 (B9) | 1 | CCRC 15527 |
| *E. coli* O103:K:H8 | 1 | CCRC 15529 |
| *E. coli* O111a, 111b:K58:H21 | 1 | CCRC 15530 |
| *E. coli* O116:K:H10 | 1 | CCRC 15531 |
| *E. coli* O120:K:H6 | 1 | CCRC 15532 |
| *E. coli* C125a, 125c:K70 (B15):H | 1 | CCRC 15533 |
| *E. coli* C128a, 128b:K67 (B12):H | 1 | CCRC 15534 |
| *E. coli* O138:K81 (B):H14 | 1 | CCRC 15535 |
| *E. coli* O142:K86 (B):H6 | 1 | CCRC 15536 |
| *E. coli* C18a, 18c:K77 (B21):H7 | 1 | CCRC 15869 |
| *E. coli* O30:K:NM | 1 | CCRC 15870 |
| *E. coli* O81:K:NM | 1 | CCRC 15872 |
| *E. coli* O83:K:H31 | 1 | CCRC 15873 |
| *E. coli* O86:K61 (B7) | 1 | CCRC 15874 |
| *E. coli* O86a:K61 | 1 | CCRC 15875 |
| *E. coli* O91:K:NM | 1 | CCRC 15876 |
| *E. coli* O101:K—:K99 | 1 | CCRC 15877 |
| *E. coli* O10:KS (L):H4 | 1 | CCRC 15878 |
| *E. coli* C112a, 112b:K68 (B13) | 1 | CCRC 15879 |
| *E. coli* 0125a, 125b:K70 (B15):H | 1 | CCRC 15880 |
| *E. coli* C128a, 128c:K67 (B12):H | 1 | CCRC 15881 |
| *E. coli* O129:(K):H11 | 1 | CCRC 15882 |
| *E. coli* O4 | 1 | CCRC 15924 |
| *E. coli* O7:K1 (L):NM | 1 | CCRC 15925 |
| *E. coli* O8:K8 (L):H4 | 1 | CCRC 15926 |
| *E. coli* O9:K9(B):H12 | 1 | CCRC 15927 |
| *E. coli* O11:K10 (L):H10 | 1 | CCRC 15928 |
| *E. coli* O12:K5 (L):NM | 1 | CCRC 15929 |
| *E. coli* O15 | 2 | CCRC 1593014 1 |
| *E. coli* O16:K92:H— | 1 | CCRC 15932 |
| *E. coli* O18 | 1 | CCRC 15933 |
| *E. coli* O21:K20 (L):NM | 1 | CCRC 15934 |
| *E. coli* O24 | 1 | CCRC 15935 |
| *E. coli* O25 | 1 | CCRC 15936 |
| *E. coli* O27:K:NM | 1 | CCRC 15937 |
| *E. coli* O28 | 1 | CCRC 15938 |
| *E. coli* O38:K:H26 | 1 | CCRC 15939 |
| *E. coli* O44 | 1 | CCRC 15940 |
| *E. coli* O48 | 1 | CCRC 15941 |
| *E. coli* O73 | 1 | CCRC 15942 |
| *E. coli* O75 | 1 | CCRC 15943 |
| *E. coli* O87 | 1 | CCRC 15944 |
| *E. coli* O90 | 1 | CCRC 15945 |
| *E. coli* O102 | 1 | CCRC 15946 |
| *E. coli* O111 | 1 | CCRC 15947 |
| *E. coli* 0112a, 112c:K66 (B11):NM | 1 | CCRC 15948 |
| *E. coli* O126:K71 (B16):H | 1 | CCRC 15949 |
| *E. coli* O135:K:NM | 1 | CCRC 15950 |
| *E. coli* O139 | 1 | CCRC 15951 |
| *E. coli* O2:K7 (56) (B1):H7 | 1 | CCRC 15969 |
| *E. coli* O153:K—:H7 | 1 | CCRC 15990 |
| *E. coli* O157:K88 (:F4) ac:H19 | 1 | CCRC 15991 |
| *E. coli* (enterotoxigenic, serotype | 8 | NCHU |

TABLE 1-continued

| Microorganism | No. of Strains | Source[a] |
|---|---|---|
| unknown) | | |
| E. coli | 2 | NCHU |
| (enteroinvasive, serotype unknown) | | |
| E. coli | 1 | NCHU |
| (enteropathogenic, serotype unknown) | | |
| E. coli (food isolates, serotype unknown) | 45 | CCRC |
| E. blattae | 1 | CCRC 15589 |
| E. fergusonii | 5 | CCRC 15582–6 |
| E. hermannii | 2 | CCRC 15587–8 |
| E. vulneris | 5 | CCRC 15952–6 |
| Aeromonas schubertii | 1 | CCRC 14138 |
| Citrobacter freundii | 3 | CCRC 10637, 12291–2 |
| Enterobacter aerogenes | 1 | CCRC 10370 |
| Enterobacter cloacae | 1 | CCRC 12313 |
| Enterococcus durans | 1 | CCRC 10790 |
| Enterococcus faecalis | 1 | CCRC 10789 |
| Enterococcus faecium | 3 | CCRC 10067, 12808–9 |
| Erwinia ananas pv. ananas | 1 | CCRC 12150 |
| Erwinia chrysanthemi | 1 | CCRC 10317 |
| Klebsiella oxytoca | 1 | CCRC 10026 |
| Klebsiella pneumoniae | 5 | CCRC 10693–4, 11546, 11644, 12284 |
| subsp. pneumoniae | | |
| Morganella morganii | 1 | CCRC 11257 |
| Proteus mirablis | 2 | CCRC 10725, 10727 |
| Proteus penneri | 1 | CCRC 14123 |
| Proteus myxofaciens | 1 | CCRC 12222 |
| Proteus vulgaris | 3 | CCRC 110486, 10728, 14882 |
| Pseudomonas aeruginosa | 1 | CCRC 11633 |
| Pseudomonas aureofaciens | 1 | CCRC 11057 |
| Pseudomonas mendocina | 1 | CCRC 10458 |
| Pseudoinonas vesicularis | 1 | CCRC 11012 |
| Salmonella arizonae | 1 | CCRC 10742 |
| Salmonella dublin | 1 | CCRC 13852 |
| Salinonella enteritidis | 1 | CCRC 10744 |
| Salmonella paratyphi A | 1 | CCRC 14878 |
| Salmonella paratyphi B | 1 | CCRC 14879 |
| Salmonella typhi | 1 | CCRC 12948 |
| Salmonella typhimurium | 1 | CCRC 12459 |
| Serratia grimesii | 1 | CCRC 10767 |
| Serratia odoriffera | 1 | CCRC 12223 |
| Serratia plymuthica | 1 | CCRC 12224 |
| Shigella boydii | 6 | CCRC 10771, 15957–61 |
| Shigella dysenteria | 1 | CCRC 13983 |
| Shigella flexneri | 3 | CCRC 10772, 13984, 15962 |
| Shigella sonnei | 3 | CCRC 10773–4, 15966 |
| Vibrio parahaemolyticus | 5 | CCRC 12863–4, 13023, 13025, 13027 |
| Yersubua enterocolitica | 1 | CCRC 139999 |

[a]ATCC, American Type Culture Collection, Rockville, Maryland, U.S.A.
CCRC, Culture Collection and Research Center, Hsinchu, Taiwan, R.O.C.
NCHU, National Chung-hsing University, Taichung, Taiwan, R.O.C.
NLFD, National Laboratories of Food and Drugs, Taipei, Taiwan, R.O.C.
NTU, National Taiwan University, Taiwan, R.O.C.

Procedures of the Conductance Method

Bacterial strains were grown on MacConkey sorbitol agar medium at 35° C. for 18 to 24 hrs. The ability of each strain to ferment sorbitol was recorded: colonies of a strain capable of fermenting sorbitol are red, whereas colonies of a strain incapable of fermenting sorbitol are white. A single colony of each strain was suspended in 10 ml of 0.1% peptone water (approximately $10^7$ cfu/ml) and serially diluted 1:10 with the same peptone water. AR1 phage was prepared with a method used for λ phage isolation (Sambrook et al., Molecular Cloning: A Laboratory Manual, 2nd Ed., Cold Spring Harbor Laboratory Press, Cold Spring Harbor, New York, 1989), and serially diluted 1:10 in a phage buffer (Ronner et al., J. Food Prot. 53:944–947, 1990). Titer of the phage was determined with a plaque assay (Snustad et al., Genetics Experiments with Bacterial Viruses, W. H. Freeman and Company, San Francisco, Calif., 1971). Conductance measurement was performed with the Malthus 2000 microbiological analyzer (Malthus Instruments, Crawley, UK). The conductivity cell was a 10-ml tube fitted with platinum electrodes printed on a ceramic base. Each tube containing 5 ml of SPYE broth was inoculated with 0.5 ml of the bacterial suspension and 0.5 ml of the phage suspension. The tubes were incubated in the Malthus analyzer at 35° C., and conductance change in each tube was automatically scanned at 6-min intervals for 22 h. Readouts were available in numerical or graphic form. The analyzer automatically determined in each tube the time point when an accelerating increase in conductance occurred, i.e., when the conductance increased 1 µS or more for three consecutive readings. This time point is termed "detection time." One hundred and twenty samples can be analyzed simultaneously by the instrument.

Definition of Positives, Negatives, Test Sensitivity, and Specificity

An E. coli isolate having white colonies on MacConkey sorbitol agar and having no detection time within 22 h was considered E. coli O157:H7 and was defined as a positive. An E. coli isolate having red colonies on McConkey sorbitol agar and having detection time within 22 h was not considered E. coli O157:H7 and was defined as a negative. The sensitivity of the conductance method was defined as the percentage of E. coli O157:H7 strains that were found to be a positive by the method. The specificity was defined as the percentage of non-O157:H7 E. coli strains that were found to be a negative (McClure, J. Assoc. Off. Anal. Chem. 73:953–960, 1990).

Optimization of the Conductance Method

Operation parameters (e.g., inoculation concentration of bacterial cells, and cell to phage ratio) were evaluated prior to a large scale of test. In the absence of AR1 phage, both E. coli CCRC 13095 (an O157:H7 strain) and E. coli CCRC 15990 (a non-O157:H7 strain) displayed similar patterns of conductivity change during the course of culturing. Further, for both strains, detection times were inversely proportional to the inoculation levels. At inoculation concentrations between $10^6$ and $10^7$ cfu/ml, the detection times were less than 3 h.

Figure 2:
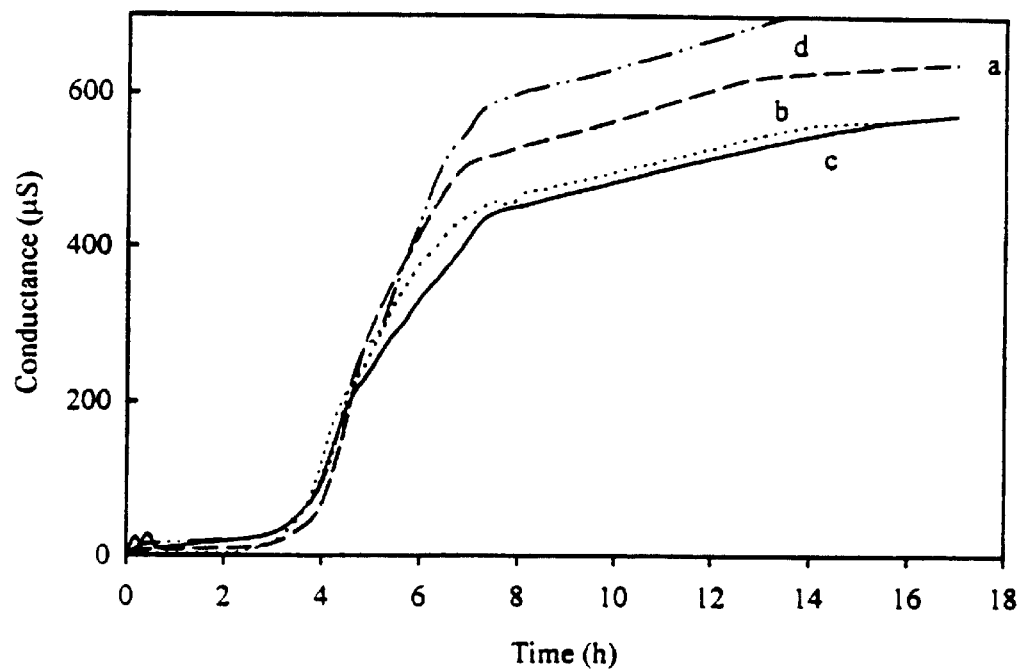
FIG. 2 is a graph showing the effect of cell:phage ratio on the conductance curves of non-O157:H7 *E. coli* (CCRC15990). Curve (a) was obtained in the absence of phage; and the remaining curves were obtained at the following cell:phage ratios: (b) 1:1, (c) 1:10, and (d) 1:100.

When AR1 phage was added to the medium inoculated with E. coli, however, great difference was observed in detection times between O157:H7 E. coli and non-O157:H7 E. coli strains. Table 2 shows the effect of various E. coli inoculation concentrations and cell to phage ratios on the detection time. When the inoculation concentration was between $10^6$ and $10^7$ cfu/ml, there was a significant increase in the detection time of E. coli O157:H7 (CCRC 13095) at a cell:phage ratio of 1:0.1 as compared to a cell:phage ratio of 1:0.01 or higher. At a cell:phage ratio of 1:10, no detection time was obtained over an incubation period of 22 h, indicating that growth of the bacteria was completely inhibited. In contrast, the detection times of non-O157:H7 E. coli remained unchanged even at a cell:phage ratio of 1:100. FIGS. 1 and 2 illustrate the changes of the conductance curves (or the detection times) of E. coli CCRC 13095 (O157:H7) and of E. coli CCRC 15990 (non-O157:H7) in the presence of AR1 phage. Specifically, the detection time of E. coli CCRC 13095 was 1.7 h in the absence of AR1 phage, and was 1.7, 16.4, >24, and >24 h when the cell-:phage ratio was 1:0.01, 1:0.1, 1:1, and 1:10, respectively.

The detection time of *E. coli* CCRC 15990, on the other hand, was 2.6 h in the absence of phage, and was 2.6, 2.6 and 2.7 h when the cell:phage ratio was 1:1, 1:10, and 1:100, respectively.

An inoculation concentration of $10^7$ cfu/ml (which can be achieved by suspending a single colony in approximately 10 ml of 0.1% peptone water) was used for the test of other bacteria. In addition, to achieve a complete growth inhibition for *E. coli* O157:H7, a cell;phage ratio of 1:10 was used for further studies. Under these conditions, detection times of non-*E. coli* O157:H7 bacteria would be obtained within a few hours, while no detection time would be obtained within 22 h for *E. coli* O157:H7 strains.

TABLE 2

Effect of cell:phage ratio on the detection times of *E. coli* O157:H7 (CCRC 13095) and of non-0157:H7 *E. coli* (CCRC 15990)[a]

| Micro-organism | Cell: phage ratio | Detection time (h) Inoculation concentration of bacterium (cfu/ml) | | | |
|---|---|---|---|---|---|
| | | $10^4$ | $10^5$ | $10^6$ | $10^7$ |
| *E. coli* CCRC 15990 (non-0157:H7) | —[b] | 4.7 ± 0.1 | 3.6 ± 0.3 | 2.6 ± 0.3 | ND[c] |
| | 1:1 | 5.0 ± 0.1 | 3.6 ± 0.2 | 2.6 ± 0.1 | ND[c] |
| | 1:10 | 4.8 ± 0.1 | 3.5 ± 0.1 | 2.7 ± 0.1 | ND[c] |
| | 1:100 | 4.7 ± 0.1 | 3.8 ± 0.2 | 2.8 ± 0.1 | ND[c] |
| *E. coli* CCRC 13095 (O157:H7) | —[b] | 5.8 ± 0.5 | 4.5 ± 0.1 | 2.7 ± 0.3 | 1.7 ± 0.2 |
| | 1:0.01 | 5.9 ± 0.2 | 4.1 ± 0.1 | 3.0 ± 0.2 | 1.7 ± 0.2 |
| | 1:0.1 | 5.7 ± 0.2 | 4.3 ± 0.2 | 14.5 ± 0.1 | 16.4 ± 3.0 |
| | 1:1 | 6.0 ± 0.3 | —[d] | —[d] | —[d] |
| | 1:10 | —[d] | —[d] | —[d] | —[d] |
| | 1:100 | —[d] | —[d] | —[d] | —[d] |

[a]Mean of triplicate ± standard deviation
[b]No phage was added to the conductance tube.
[c]Not determined.
[d]No detection time.

Identification of *E. coli* O157:H7

The optimal conditions for the conductance method as described above were applied to test a total of 269 bacterial strains (Table 1). Among the 269 strains, 41 were *E. coli* O157:H7; 99 were *E. coli* having serotypes other than O157:H7; 56 were non-O157 isolates of *E. coli* with serotypes undetermined; and 73 were other bacteria.

All 41 strains of *E. coli* O157:H7 were correctly identified: No detection times could be obtained for these strains during a 22 h incubation period (Table 3). Thus, the sensitivity of the test was 100% (41/41). Surprisingly, among the 155 non-O157:H7 *E. coli* strains, 13 were found to be positive by the conductance method, and of all these 13 false-positives, 12 were sorbitol-fermenters (i.e., red colonies on MacConkey-sorbitol agar; Table 3) with the remaining *E. coli* O125a, 125c:K70(B15):H being a sorbitol non-fermenter. In other words, a combination of the conductance test and the sorbitol fermentation test leads to a specificity as high as 99.4% (154/155) for determining if an *E. coli* isolate is O157:H7.

Four strains of Shigella spp., including one *S. boydii* (serotype 5) and two *S. flexneri* strains, produced false-positive results among the 73 strains of non-*E. coli* bacteria (Table 3). However, these bacteria were not *E. coli*, and hence there is no need to consider if they are *E. coli* O157:H7.

The main advantages of the conductance method are high sensitivity and specificity, low cost, and adaptability to automation.

TABLE 3

Colony color of bacteria grown on MacConkey sorbitol agar and the results of conductance test.

| Microorganism | Colony color on MacConkey sorbitol agar[a] | No. of strain | Result of conductance test[b] + | Result of conductance test[b] − |
|---|---|---|---|---|
| *E. coli* O157:H7 | W | 41 | 41 | 0 |
| non-O157:H7 *E. coli* (serotypes determined) | R | 87 | 5 | 82 |
| | W | 12 | 1 | 11 |
| non-O157:H7 *E. coli* (serotypes unknown) | R | 50 | 7 | 43 |
| | W | 6 | 0 | 6 |
| *Escherichia blattae* | W | 1 | 0 | 1 |
| *Escherichia fergunsonii* | W | 5 | 0 | 5 |
| *Escherichia hermannii* | W | 2 | 0 | 2 |
| *Escherichia vulneris* | W | 5 | 0 | 5 |
| *Aeromonas schubertii* | No growth | 1 | 0[e] | 0[e] |
| *Citrobacter freundii* | R | 3 | 0 | 3 |
| *Enterobacter* spp. | R | 2 | 0 | 2 |
| *Enterococcus* spp. | No growth | 5 | 0[e] | 0[e] |
| *Enteroccus* spp. | W | 1 | 0 | 1 |
| *Erwinia* spp. | W | 1 | 0 | 1 |
| | R | 1 | 0 | 1 |
| *Klebsiella* spp. | R | 6 | 0 | 6 |
| *Morganella morganii* | W | 1 | 0 | 1 |
| *Proteus* spp. | W | 5 | 0 | 5 |
| *Proteus* spp. | No growth | 2 | 0[e] | 0[e] |
| *Pseudomonas* spp. | W | 3 | 0 | 3 |
| | No growth | 1 | 0[e] | 0[e] |
| *Salmonella* spp. | R | 7 | 0 | 7 |
| *Serratia* spp. | R | 2 | 0 | 2 |
| | No growth | 1 | 0[e] | 0[e] |
| *Shigella* spp. | R | 3 | 0 | 3 |
| | W | 8 | 3 | 3 |
| | No growth | 2 | 0[e] | 0[e] |
| *Vibrio parahaemolyticus* | W | 5 | 0 | 0 |
| | W | 5[e] | 0[e] | 0[e] |
| *Yersinia enterocolitica* | R | 1 | 0 | 1 |

[a]Sorbitol-fermenters have red (R) colonies and sorbitol.non-fermenters have white (W) colonies on MacConkey sorbitol agar.
[b]"+" strain having no detection time within 22 h, "−" a strain having detection time within 22 h.
[e]Test strains failed to grow either on MacConkey sorbitol agar or in SPYE broth.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For instance, any phage that displays host specificity similar to AR1 can be used in lieu of AR1 in the present methods. Also, any analog of sorbitol and any biochemical process analogous to sorbitol fermentation can be used in lieu of sorbitol and sorbitol fermentation, respectively.

What is claimed is:

1. A method of determining whether a test microorganism is *E. coli* O157:H7, said method comprising:

providing a first culture that contains the test microorganism and bacteriophage AR1;

measuring a growth rate-related value of the first culture; and comparing the value of the first culture with a corresponding growth-rate related value of a second culture, the composition of the second culture being identical to that of the first culture except that the second culture is free of bacteriophage AR1, or contains *E. coli* O157:H7 and is free of bacteriophage AR1;

wherein a difference in the two values is an indication that the test microorganism is *E. coli* O157:H7.

2. The method of claim 1, wherein the growth rate-related value is a value of an electrical parameter, or a value derived from values of an electrical parameter.

3. The method of claim 2, wherein the growth rate-related value is a time point at which an accelerating change of the electrical parameter occurs.

* * * * *